United States Patent
Sedillo

(10) Patent No.: US 10,277,316 B1
(45) Date of Patent: Apr. 30, 2019

(54) FREE SPACE OPTICAL HEADSET

(71) Applicant: The United States of America, as represented by the Secretary of the Air Force, Washington, DC (US)

(72) Inventor: Michael R Sedillo, Dayton, OH (US)

(73) Assignee: The United States of America as Represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 15/583,311

(22) Filed: May 1, 2017

(51) Int. Cl.
| | | |
|---|---|---|
| *H04B 10/114* | (2013.01) | |
| *H04B 10/40* | (2013.01) | |
| *H04R 1/02* | (2006.01) | |
| *A61F 11/08* | (2006.01) | |
| *A61F 11/14* | (2006.01) | |

(52) U.S. Cl.
CPC ............ *H04B 10/114* (2013.01); *A61F 11/08* (2013.01); *A61F 11/14* (2013.01); *H04B 10/40* (2013.01); *H04R 1/028* (2013.01); *A61F 2011/145* (2013.01); *H04R 2499/11* (2013.01)

(58) Field of Classification Search
CPC .. H04B 10/114; H04B 10/40; H04B 10/1143; H04B 10/25758; H04B 10/25752; H04B 10/25753; H04J 14/0298; A61F 11/08; A61F 11/14; H04R 1/028
See application file for complete search history.

(56) References Cited

U.S. PATENT DOCUMENTS

| | | |
|---|---|---|
| 3,277,303 A | 10/1966 | Jensen et al. |
| 4,648,131 A | 3/1987 | Kawaguchi et al. |
| 4,882,770 A | 11/1989 | Miyahira et al. |
| 4,972,491 A | 11/1990 | Wilcox, Jr. |
| 5,027,433 A | 6/1991 | Menadier et al. |

(Continued)

FOREIGN PATENT DOCUMENTS

| | | |
|---|---|---|
| EP | 1484852 A2 | 12/2004 |
| WO | 0249324 A1 | 6/2002 |

OTHER PUBLICATIONS

Buchholz, et al.; Optically Driven Wireless Earplug for Communications and Hearing Protection; pp. 1-8; Published in the Proceedings of the Forty Third Annual SAFE Association Symposium, Salt Lake City, Utah, Oct. 24-26, 2005.

*Primary Examiner* — Ted M Wang
(74) *Attorney, Agent, or Firm* — AFMCLO/JAZ

(57) ABSTRACT

A communications headset system and method of use utilizing first and second headsets with integrated hearing protection for enabling users to wirelessly communicate when the hearing protection is engaged. Each headset is configured for placement onto a user's head and includes hearing protection cups that engage a user's ears and attenuate incoming sound waves external to the headset. The headsets include a first optical receiver that detects a light signal within a first receiving field-of-view and generates an incoming electrical signal corresponding to the light signal. A speaker converts the incoming electrical signal to an incoming audio signal, and then outputs the incoming audio signal as sound waves. A microphone converts outgoing sound waves to an outgoing electrical signal. An optical transmitter converts the outgoing electrical signal to one or more light signals and then broadcasts the one or more light signals within a broadcast field-of-view and a broadcast range.

9 Claims, 11 Drawing Sheets

(56) References Cited

U.S. PATENT DOCUMENTS

| | | | |
|---|---|---|---|
| 5,095,382 A * | 3/1992 | Abe | H04B 10/114 |
| | | | 320/107 |
| 5,426,719 A | 6/1995 | Franks et al. | |
| 5,455,702 A | 10/1995 | Reed et al. | |
| 5,748,813 A | 5/1998 | Cassidy et al. | |
| 6,788,901 B2 | 9/2004 | Sidorovich et al. | |
| 6,795,655 B1 | 9/2004 | Sidorovich et al. | |
| 6,829,439 B1 | 12/2004 | Sidorovich et al. | |
| 6,893,346 B2 | 5/2005 | Small et al. | |
| 6,965,713 B2 | 11/2005 | Sidorovich | |
| 6,968,062 B1 | 11/2005 | Inanaga | |
| 7,072,475 B1 | 7/2006 | DeNap et al. | |
| 7,079,774 B2 | 7/2006 | Sidorovich et al. | |
| 7,099,589 B1 | 8/2006 | Hiramatsu | |
| 7,457,428 B2 | 11/2008 | Vaudrey et al. | |
| 8,243,943 B2 | 8/2012 | Nordin et al. | |
| 8,774,060 B2 | 7/2014 | Bryant | |
| 2003/0142841 A1 | 7/2003 | Wiegand | |
| 2004/0208603 A1 * | 10/2004 | Hekkel | H04B 10/1125 |
| | | | 398/140 |
| 2005/0260953 A1 * | 11/2005 | Lefler | H04B 1/385 |
| | | | 455/100 |
| 2008/0175406 A1 * | 7/2008 | Smith | H04R 1/1066 |
| | | | 381/87 |
| 2009/0041285 A1 * | 2/2009 | Parkins | A61F 11/08 |
| | | | 381/372 |
| 2010/0142722 A1 | 6/2010 | Von Wiegand | |
| 2012/0263478 A1 | 10/2012 | Jang | |
| 2013/0064552 A1 | 3/2013 | Fortune et al. | |

* cited by examiner

FREE SPACE OPTICAL HEADSET

GOVERNMENT INTEREST

The invention described herein may be manufactured and used by or for the Government of the United States for all governmental purposes without the payment of any royalty.

FIELD OF THE INVENTION

This invention relates to the field of hearing protection. More particularly, this invention relates to a hearing protection system that enables selective communication between a plurality of users using free-space optics, particularly in noisy environments.

BACKGROUND OF THE INVENTION

Hearing protection devices are often worn to mitigate the impact of excessive noise. Depending on the noise level, hearing protection is often layered to provide necessary additive protection. Earplugs are frequently used as either a baseline protective layer, or in conjunction with over-the-ear earmuffs for additional layers of protection. More advanced technological innovations include the use of active noise reduction (ANR) systems that use microphones to sample the offending noise and transmit sound-cancelling noise to reduce the noise-levels reaching the inner ear, thus providing even higher levels of hearing protection when used with earplugs and over-the-ear muffs. These protective measures are very effective at significantly reducing ambient noise reaching the user's ears, but, for the same reason, may hamper communication between users unless supplementary communication techniques are used.

Radio-frequency (RF) communication is highly effective in transmitting messages long distances, through structures, and to large groups of people who are omni-directionally dispersed. However, RF communications require users to switch to private channels for communications that they do not want transmitted to everyone who may be monitoring the same radio channel. Participants in the "private conversation" need to physically switch their radios to this private channel to communicate privately, and then switch back to the common frequency for general communication with everyone else. This is cumbersome when short messages are conveyed face-to-face during high-tempo activities such as preparing to launch aircraft, in-flight patient care, or during manufacturing operations that take place in high-noise environments.

Often, personnel working in high-noise environments, such as in the flight industry, use hearing protection without radios. Radios are typically reserved for personnel who need to communicate directly with the aircraft or other control agencies. Aboard aircraft carriers, hand-signals are used to communicate basic messages using a known, specific hand-signal language. Problems occur when the message is outside the known vocabulary or if trying to communicate with someone not trained in the hand-gesture language. When more elaborate communication is required between personnel without radio-equipped headsets, or to convey a message not part of the hand-gesture vocabulary, these personnel often approach each other and yell their messages to overcome the high-noise environment and to penetrate the hearing protection the recipient is wearing.

In these instances, it is typically difficult to understand the message and the information is not effectively transmitted. This might result in the recipient lifting their hearing protection off their ears to allow the verbal message to be more easily understood. However, by removing their hearing protection, they expose their ears to the high noise.

Additionally, there are hazardous conditions where radio transmissions are prohibited, such as when working with open fuel-tanks or near explosives, when electromagnetic energy or radio-frequency (RF) emissions could cause an explosion. Similarly, when sensitive electronic equipment is present, such as aircraft avionics, RF wireless headsets are not permitted due to the potential of electromagnetic interference.

Therefore, what is needed, is a hearing protection and communications module that overcomes the deficiencies described above.

SUMMARY OF THE INVENTION

The above and other needs are met by a communications headset system having first and second headsets with integrated hearing protection for enabling users to wirelessly communicate when the hearing protection is engaged. Each headset is configured for placement onto a user's head and includes hearing protection cups mounted to the headset and configured to engage a user's ears and to attenuate incoming sound waves that are external to the headset. The headsets further include a first optical receiver that detects a light signal within a first receiving field-of-view and generates an incoming electrical signal that corresponds to the light signal. A speaker is in electrical communication with the first optical receiver and converts the incoming electrical signal to an incoming audio signal. The speaker then outputs the incoming audio signal as sound waves. A microphone receives and converts outgoing sound waves to an outgoing electrical signal. An optical transmitter in electrical communication with the microphone receives and converts the outgoing electrical signal to one or more light signals and then broadcasts the one or more light signals within a broadcast field-of-view and a broadcast range.

Certain embodiments further include a second optical receiver having a second receiving field-of-view that is at least partially outside of the first receiving field-of-view. The second optical receiver detects the one or more light signals within the second receiving field-of-view and generates the incoming electrical signal therefrom. In some cases, the first receiving field of view is forward-facing and the second receiving field-of-view is rearward-facing. In some cases, the secondary optical receiver includes an optical detector, a dome optic mounted over the receiver, and a cone reflector mounted within the dome optic and above the optical receiver. The one or more light signals pass through the dome optic so as to be reflected off of the cone reflector into the optical detector.

Certain embodiments further include an amplifier for selectively increasing or decreasing the broadcast range of the optical transmitter. The optical transmitter may be configured to incorporate a signal boost indicator into the one or more light signals when the amplifier selectively increases the broadcast range beyond a default range. In some cases, the headsets may include a visual indicator that is viewable when the signal boost indicator is received by the headset. In some cases, the optical transmitter automatically increases the broadcast range of the one or more light signal using the amplifier in response to the first optical receiver receiving the signal boost indicator.

Certain embodiments further include secondary hearing protection located within each of the hearing protection cups of the headsets. In certain cases, a speaker is integrated into the secondary hearing protection.

Some embodiments include an integrated mask that selectively engages a mouth of the user for attenuating incoming sound waves external to the mask, wherein the microphone is disposed within the mask. In some preferred embodiments, the headsets further include a push-to-talk button for selectively activating the microphone.

In certain cases, the optical transmitter is selectively configurable by the user to transmit the one or more light signals using one or more light sources operating at at least one of a plurality of wavelengths. In some preferred embodiments, the headset is selectively configurable to generate an incoming electrical signal when the one or more light signals is at one or more selected wavelengths.

BRIEF DESCRIPTION OF THE DRAWINGS

Other embodiments of the invention will become apparent by reference to the detailed description in conjunction with the figures, wherein elements are not to scale so as to more clearly show the details, wherein like reference numbers indicate like elements throughout the several views, and wherein.

DETAILED DESCRIPTION OF THE INVENTION

Free-space optics (FSO) transceivers can wirelessly transmit large amounts of data using fast-pulsing light emitting diodes (LED) creating broad-beam, duplex transmission between transceivers. FSO transceivers can vary their transmission fields-of-view and range by either tuning the optics or by varying the power applied to the LEDs. Additionally, the reception field of view may be varied by varying the type and number of active and inactive receivers. By aiming corresponding FSO transceivers in the general direction of each other, a broadband, full duplex connection is quickly established if the transceivers can optically "see" each other and if they are within range of each other. The communication link is exclusive to recipients in the FSO field-of-view and within the range of the light signal.

As used herein, the term "speaker" means any listening device or electroacoustic transducer that converts an electrical signal into sound waves, including, for example, headphones, in-ear monitors, earbuds, bone conduction transmitters, and the like. As used herein, the term "microphone" means any electroacoustic transducer that converts sound waves into an electrical signal.

Figure 1:
FIG. 1 depicts a communications headset system in use by several users according to an embodiment of the invention.

With initial reference to FIG. 1, there is provided a communications headset system 100 for providing wireless duplex communication between two or more users. The system 100 enables selective communication between two users (i.e., one-to-one) or between a plurality of users (i.e., one-to-many) using free-space optics. The system 100 includes two or more headsets 102, each having integrated hearing protection and communications modules that utilize free-space optics for forming a communications link to enable simplex or duplex communication between a pair of users or between multiple users. As discussed in greater depth below, the headsets 102 enable users to wirelessly communicate with one another without removing the hearing protection. Another advantage of this system 100 is that users' messages are transmitted using light signals and not radio waves. This obviates any concerns that RF energy may interfere with any sensitive electronics nearby, such as avionics systems, or that sensitive information will be omnidirectionally transmitted with respect to the sender.

Figure 2:
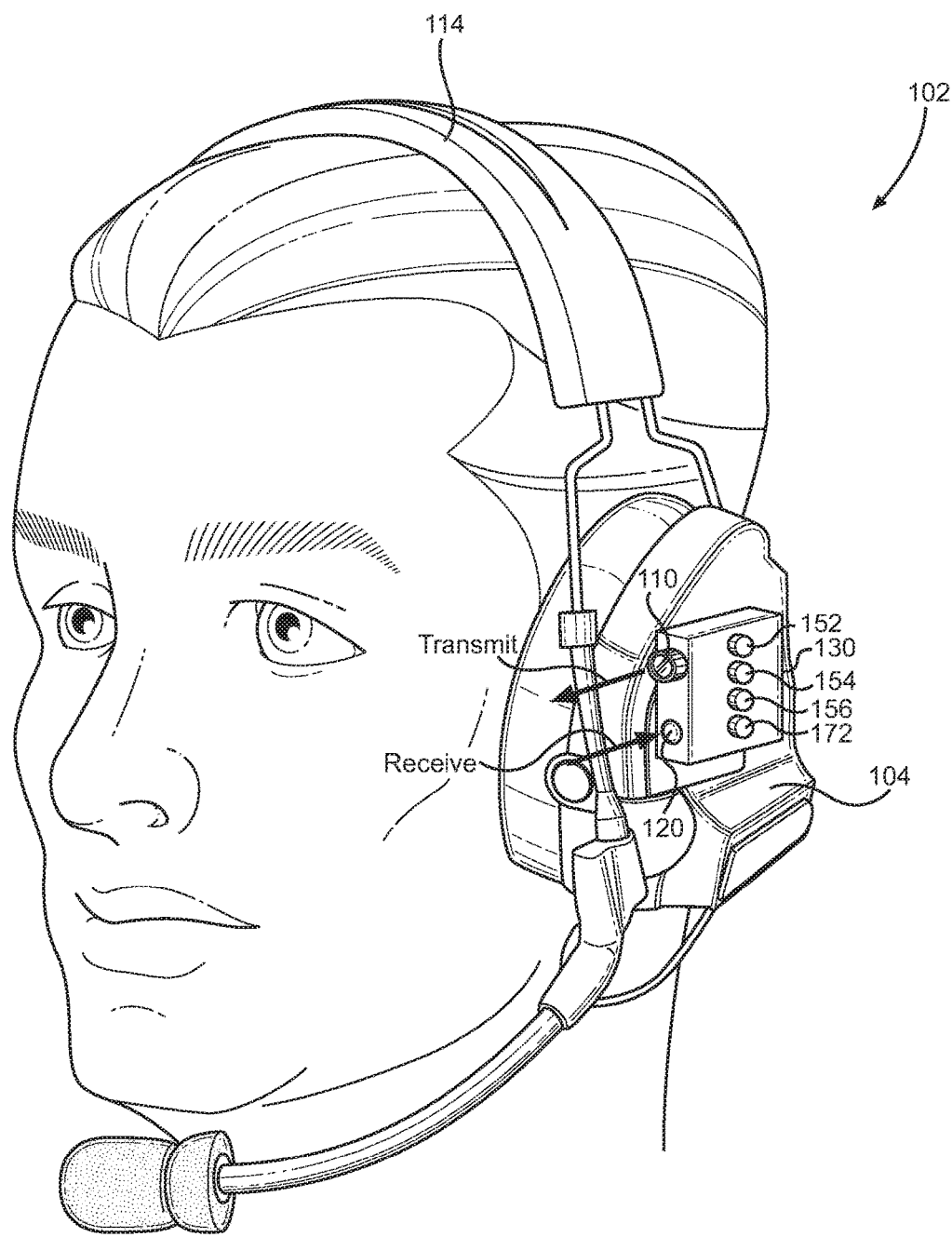
FIG. 2 depicts a headset with integrated hearing protection for enabling users to wirelessly communicate with one another according to an embodiment of the invention.
Figure 3:
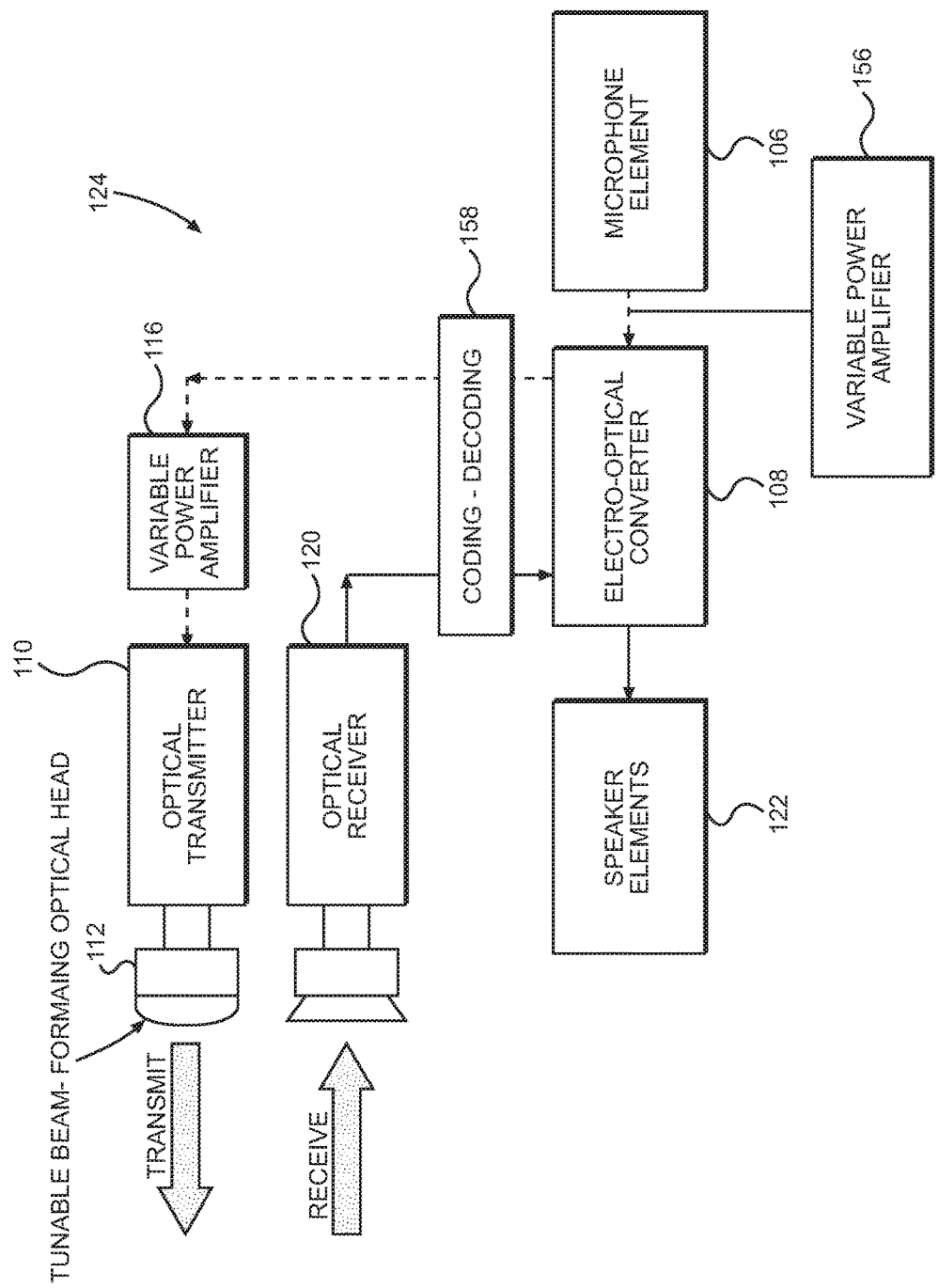
FIG. 3 is a functional block diagram of a headset with integrated hearing protection according to an embodiment of the invention.

As shown in FIGS. 2 and 3, each headset 102 can have hearing protection mounted to the headset that is configured to engage a user's ears and to attenuate incoming sound waves external to the hearing protection. An advantage of this design is that users can easily communicate with one another while the headset 102 and hearing protection remain in place. In this case, the headset 102 includes hearing protection cups 104 that engage the user's ears. The hearing protection cups 104 are mounted to a tension headband 114 to provide the desired hearing protection. In addition to the hearing protection discussed above, each headset 102 can include a communications module 124 that enables users to transmit audio messages to other users and to also receive audio messages from other users using free-space optics. It will be appreciated that in other embodiments, the hearing protection and communications modules 123 may be integrated into a hat, a helmet, or any other type of headgear.

The message transmission function of the communications module 124 is provided by a microphone 106, an electro-optical converter 108, a front-facing optical transmitter 110, a beam-forming optical head 112, and optionally a variable power amplifier 116. The message reception function is provided by a front-facing optical receiver 120, the electro-optical converter 108, and speaker 122.

Turning first to the message transmission function of the headset 102, when a user wants to communicate with another user, he provides an incoming audio signal by speaking into the microphone 106. In some embodiments, the microphone 106 is active only when the user holds a push-to-talk (PTT) button 152 located on the headset. However, in other cases, the user may override this function (such as by toggling the PTT button 152 or another on-headset "hot mic" button) such that the headset 102 remains active without further input from the user. The microphone 106 converts the sound waves of the incoming audio into a corresponding analog signal, which analog signal is then digitized by the electro-optical converter 108 to a digital signal. The analog signal provided by the microphone 106 may optionally be boosted by an amplifier 156 prior to conversion by the electro-optical converter 108. This may be particularly useful for improving weak or noisy signals. The digital signal provided by the electro-optical converter 108 is then output as a light signal by the optical transmitter 110.

The light signal comprises a series of light pulses that propagate in free space. In some embodiments, a variable power amplifier 116 may be provided to selectively increase or decrease the effective range of the light signal. This amplifier 116 may be selectively operated by a power boost button 154, which may be located on the headset 102. Additionally, as discussed further below, in some embodiments, the power boost may automatically boost the transmitted light signal when the headset 102 receives a boosted signal from another headset.

Figure 10:
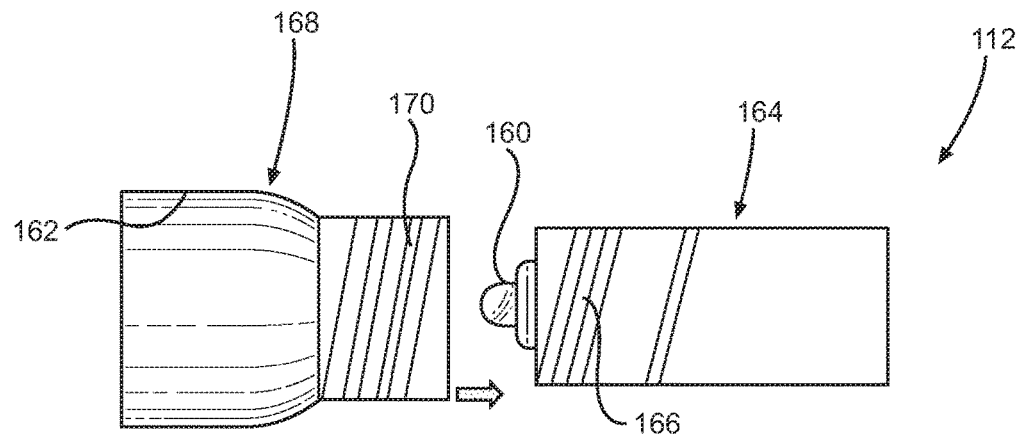
FIGS. 10-12 depict a tunable beam-forming optical head according to an embodiment of the present disclosure.
Figure 11:
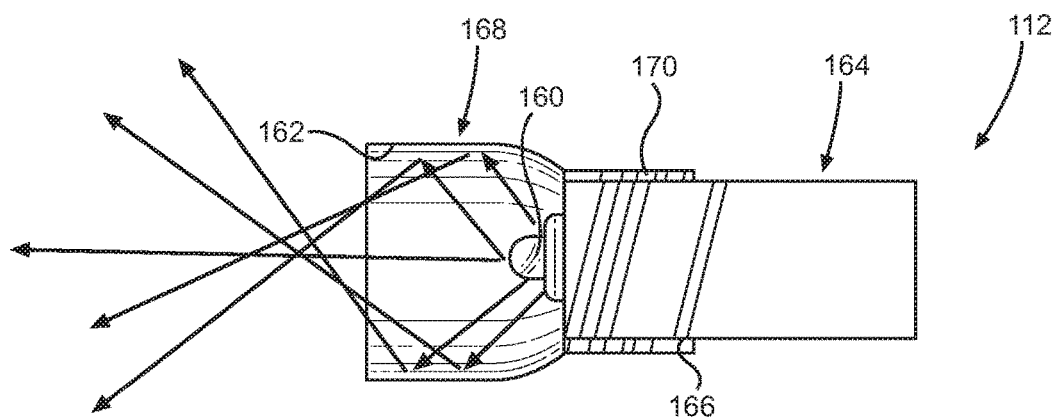
Figure 12:
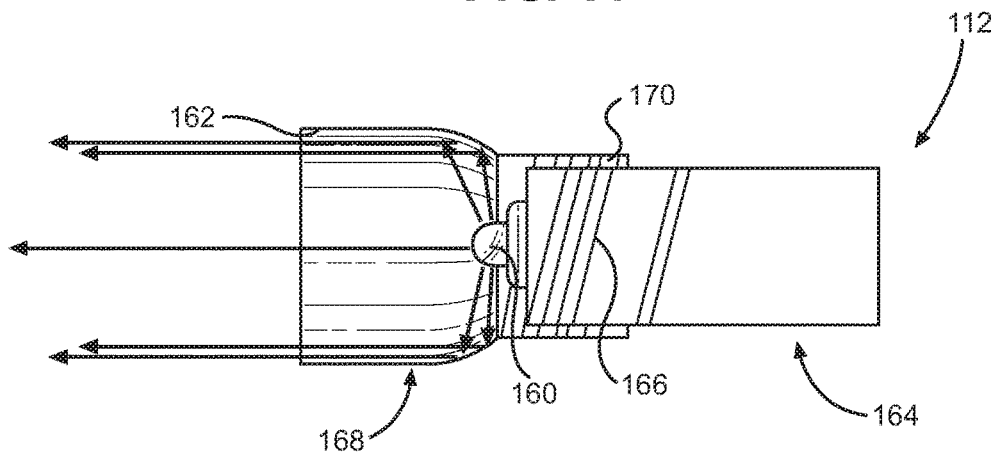

Additionally, the optical head 112 can be equipped with adjustable beam-forming optics that enables the beam width and effective range to be increased or decreased. One example structure for achieving this type of adjustability is illustrated in FIGS. 10-12. As illustrated, the beam-forming optics 112 include a light source 160 mounted to a first housing section 164 having a first threaded interface 166. A reflector 162 (a reflective surface in this case) is located inside of a second housing section 168 having a second threaded interface 170. The housing sections 164, 168 are connected together by engaging the first threaded interface 166 with the second threaded interface 170. The reflector 162 focuses light emitted by the light source 160 by moving the second housing section 168 and the reflector with respect to the first housing section 164 and the light source. In the illustrated embodiment, this is accomplished by turning the first threaded interface 168 with respect to the second threaded interface 170 to cause housing sections 164, 168 to move towards or away from one another. It will be appreciated that a variety of other beam-forming optics can be adapted for purposes of the present invention. One such structure for making the adjustments described above, for example, is disclosed in U.S. Pat. No. 9,022,610.

Turning now to the message reception function of the headset 102, a light signal is detected by the front-facing optical receiver 120. The electro-optical converter 108 then converts the light signal into an electrical signal, which can be output as an audio signal or sound waves via the speakers 122. The speakers 122 are mounted to the headset 102 and are positioned so that the user can hear the audio signal while the hearing protection cups 104 remain engaged.

A communications link is established when a light signal is received by the front-facing optical receiver 120 of another headset 102. A one-way communications link (i.e., simplex) is established when a first user wearing a headset 102 can successfully transmit a message to second user wearing a headset 102 (i.e., the second user receives the message), but the second user cannot successfully transmit a message back to the first user. A two-way communications link (i.e., duplex) is established between the first and second users when communications sent by either user can be successfully received by the other user.

Figure 4:
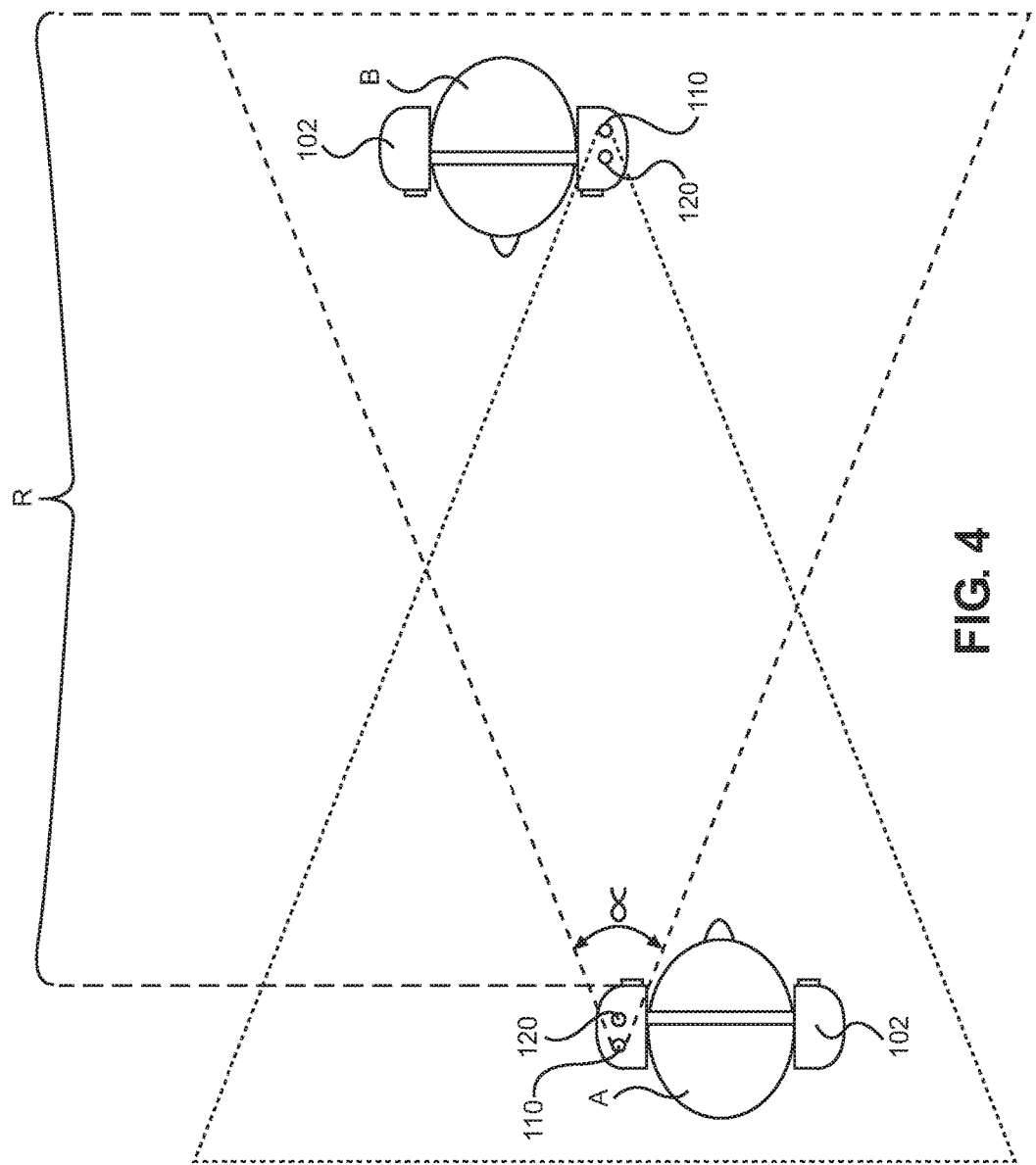
FIG. 4 is a depiction of two users wearing headsets where a two-way communications link has been established between them.
Figure 6:
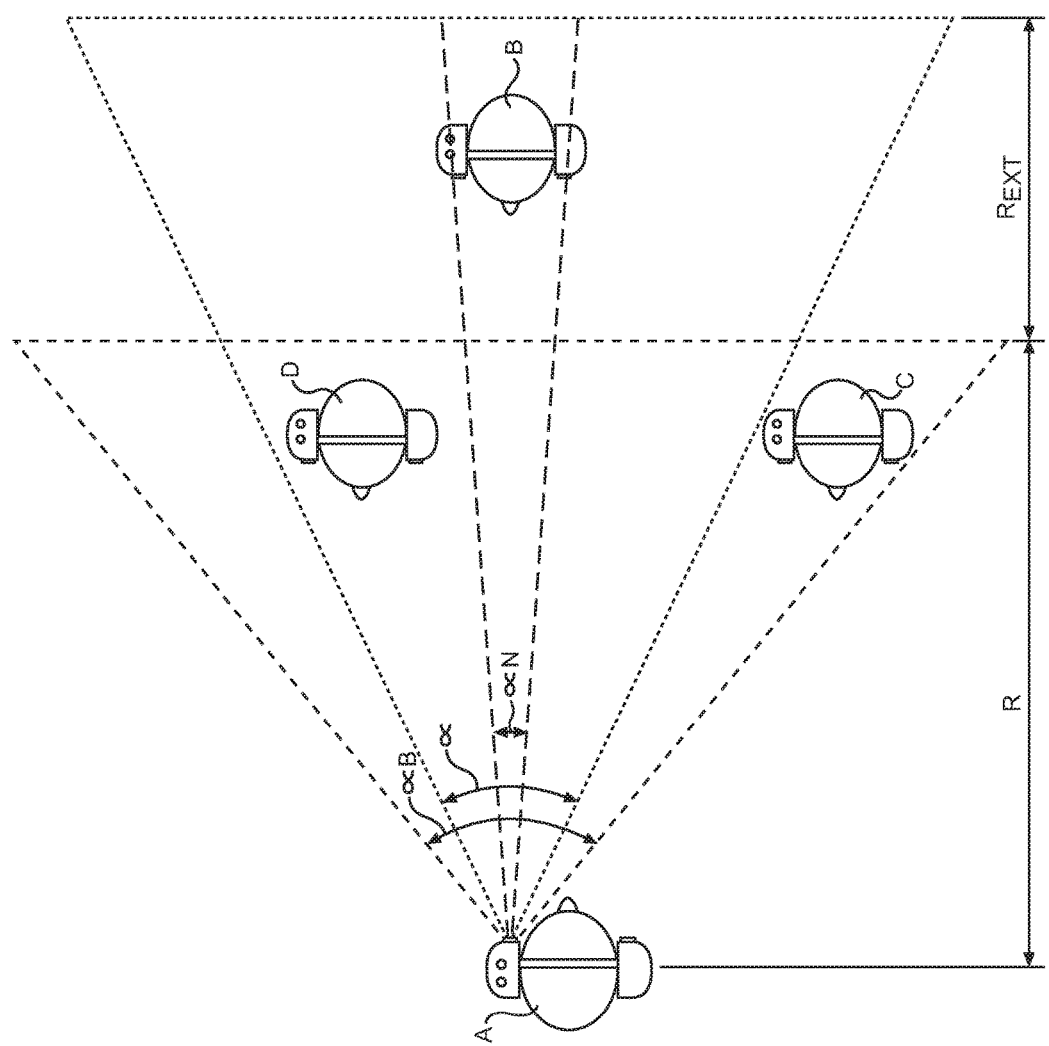
FIG. 6 is a depiction of the users in FIG. 5 where a two-way communications link has been established between them.

In FIG. 4, there is provided a depiction of a two-way communications link formed between a first user A and a second user B, where each user is wearing a headset 102 in accordance with an embodiment of the disclosed invention. The beam-forming optical head 112 of each headset 102 produces a light signal that has a range R and a field-of-view (FOV). The range R is a measurement of the distance away from the optical head 112 that the light signal can travel with sufficient intensity to be successfully received by another headset 102 and converted into an audio message. This distance depends on several factors, including the intensity of the light source, beam angle, and atmospheric conditions, and may range from several hundred feet to several miles. The FOV is the broadcast angle α of the light signal produced by the light source measured in degrees. In the illustrated embodiment, the FOV produced by the single light source in the optical head 112 has an angle α of about 45°. As discussed above, in some embodiments, the FOV may be changed through a variety of beam-forming optics, such as by varying the distance between the light reflector 162 and the light source 160 as illustrated in FIGS. 10-12. Varying the distance between the light reflector 162 and the light source 160 can cause the beam angle α to be increased or decreased, which has an inverse relationship with range R, as shown in FIG. 6. As the beam angle α increases, the light signal becomes less intense and the range R is reduced. Conversely, reducing the beam angle α causes the light signal to become more intense and its range is increased.

In some embodiments, the transmitting FOV may be increased or decreased by varying the type and number of active light sources. Additionally, the receiving FOV may be increased or decreased by varying the type and number of active light receivers. Accordingly, the system 100 disclosed herein may have multiple modes of operation, including a "discovery" or "conference" mode for broadcasting and receiving signals broadly to a potentially large number of users and a "directed" or "focused" mode for broadcasting and receiving signals narrowly to a small, limited number of users.

Figure 9:
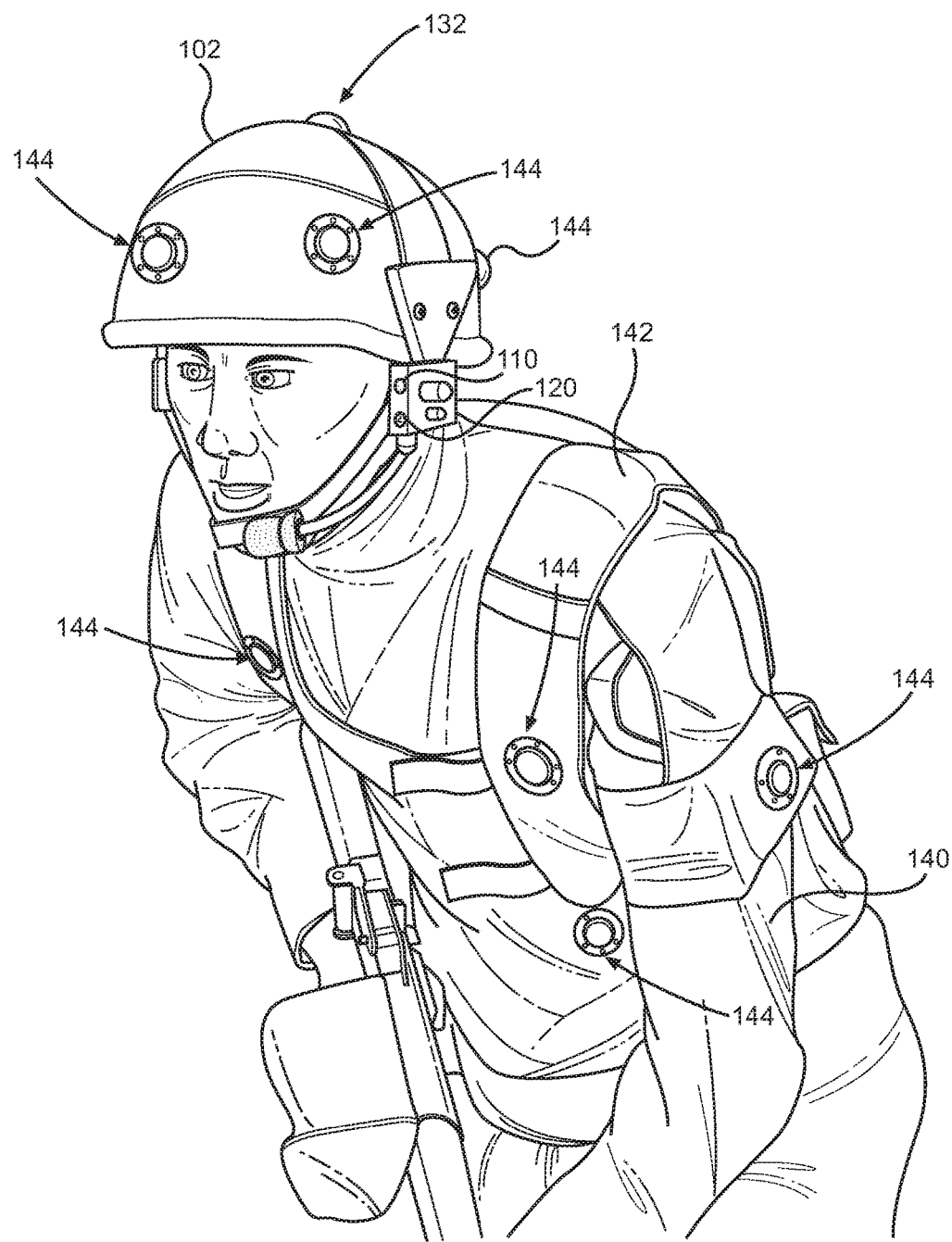
FIG. 9 depicts a user wearing headset, equipment, and apparel that is provided with a plurality of optical receivers.

In one example, the system shown in FIG. 9 is provided with multiple types of transmitters and receivers that can be configured to operate independently or in conjunction with one another. The headset 102, for example, includes the front-facing optical transmitter 110 and the front-facing optical receiver 120 discussed above. It is noted that the transmitter 110 and receiver 120 could be combined to function as a single transceiver. Due to their front-facing orientation, this combination may be beneficial in the "directed" mode for communicating with one or more users that are located substantially in front of another user. Additionally, as discussed further below, a secondary "hail" optical receiver 132 may be beneficial for receiving signals from a transmitting headset that is located behind the user. Both the headset 102 and garments 140 worn by the user may be further equipped with multiple transceivers 144 that may be configured to broadcast as well as receive light signals and that are located around the user's body to give the user omni-directional visibility when broadcasting or receiving light signals. These transceivers are useful in the "discovery" mode of operation for transmitting a signal to multiple receiver users located around the transmitting users or for communicating with a user whose exact position is not known.

It will be appreciated that using multiple receivers and transmitters requires a larger amount of energy than a smaller number of receivers and transmitters. Additionally, a wide broadcast and receiving FOV may not also be necessary or meet security or privacy needs. Therefore, the user may have the option to select the transceivers that are active via a mode selection button 172 in order to broaden or narrow the broadcast or reception FOV. For example, the user may choose to activate one or more than one transceiver, including various combinations of multiple transceivers. Those combinations may include, for example, some or all front-facing receivers, some or all rear-facing receivers, etc. The mode selection button 172 for cycling through the various modes may be located on the headset 102 (as shown in FIG. 2) or elsewhere on the user's body.

Alternatively, the system 100 may be configured to automatically select the mode of operation in order to improve power usage or increase security or privacy. For example, the discovery mode may be used initially to locate other receivers. Receiving headsets 102 may be configured to automatically send a "received signal" response back to the transmitting headset that the signal was received. Once the transmitting headset receives one or more of the "received signal" response, it may deactivate all transceivers except those needed to communicate with the user receiving their signal. The active transceivers may be continuously updated based on the number and location of "received signal" responses or other incoming transmissions. For example, if the receiving headset moves position with respect to the transmitting headset, the active transceivers of each headset may change in order to maintain a communications link.

In the embodiments discussed above, multiple transceivers 144 having multiple discrete light sources were described as varying the FOV. In an alternative embodiment, a single light source paired with a wide or ultra-wide angle lens, such as a fish eye lens, may be utilized to provide a wide field of view while, at the same time, minimizing power consumption.

Figure 5:
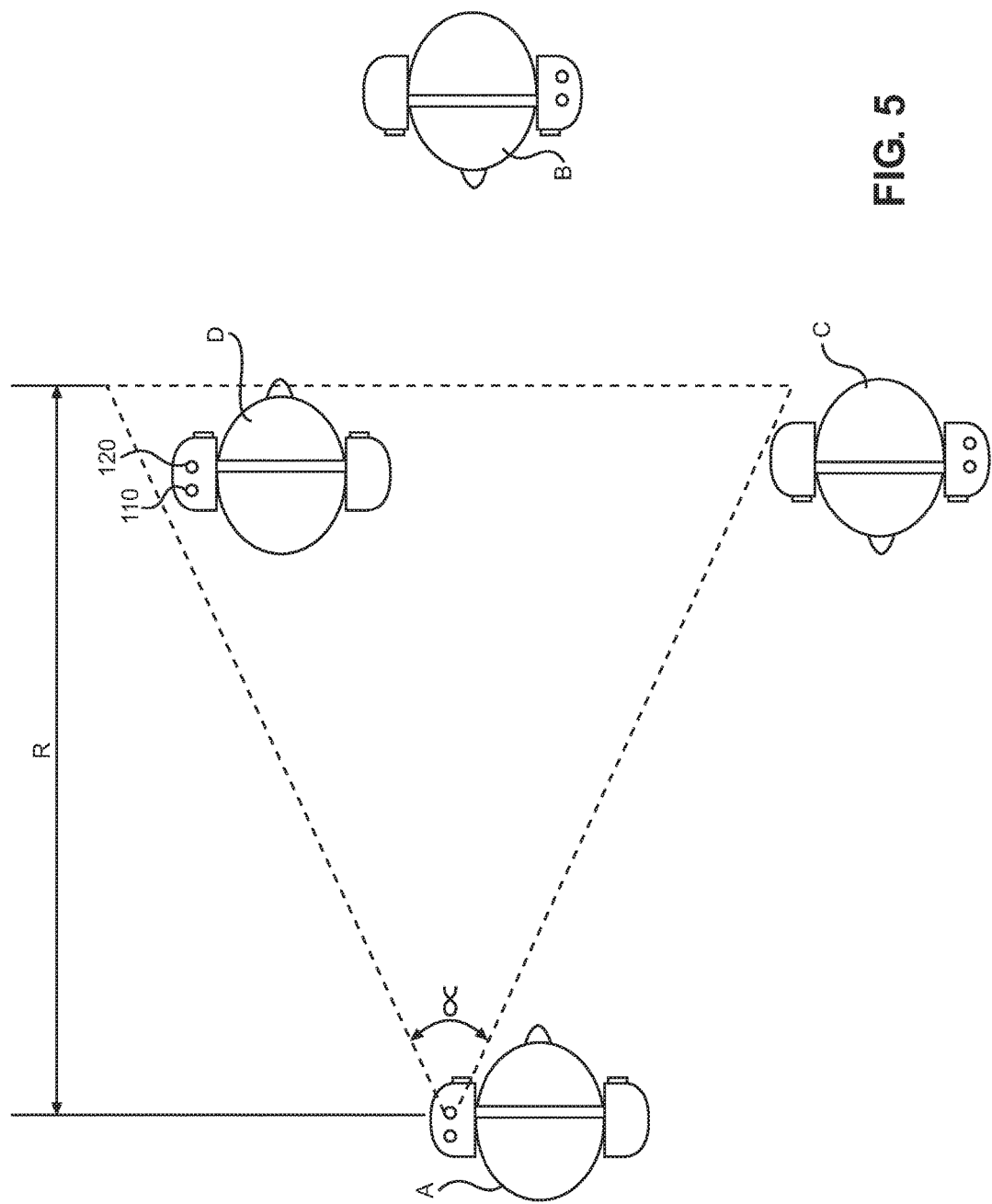
FIG. 5 is a depiction of multiple users wearing headsets where communications links have not been established between them.

FIGS. 4-6 illustrate the relevance of FOV and range R according to the embodiments described herein. In FIG. 4, User A is within the FOV and range R of the light signal produced by User B's headset 102. Additionally, User A is oriented with respect to User B such that a front-facing optical receiver 120 on User's A headset 102 can receive light emitted by User B's headset 102. Thus, at least a one-way communications link is formed and messages sent from User B can be communicated to User A. In this particular case, User B is also within the range R and FOV of the light signal of User A's headset 102 and has a correct orientation with respect to User A. Thus, a two-way communications link is formed because both users can communicate messages to the other.

FIG. 5 illustrates several example cases where a communications link is not formed. As shown in FIG. 5, when User A and User B are separated by a large distance, no communication link is formed between them. This might occur, for example, if User A moves away from User B or vice versa. Alternatively, this might occur if the beam strength is reduced such that range R is diminished. While User B is correctly oriented and is within the FOV of User A's light signal, User B is not within the range R of the light signal. Thus, no communications link is formed between User A and User B. User C is correctly oriented and is within the range R of User A's light signal, but User C is not within the FOV of User A's light signal. Lastly, User D is within the range R and FOV of User A, but User D is not correctly oriented in relation to User A. Since User D is facing away from User A, the light signal sent from User A cannot be received at User D's front-facing optical receiver 120.

FIG. 6 illustrates how the limitations noted above may be overcome using the presently-disclosed headset 102. First, in the case of User A-User B communications, a communication link may be formed by extending the range R of User A's light signal.

The range R may be extended by length REXt in at multiple ways according to various embodiments of the invention. In one embodiment, the beam angle may be reduced from angle $\alpha$ to a narrower angle $\alpha_N$. By narrowing the beam angle, the light signal becomes more intense and the range may be extended. In another embodiment, the range of the light signal can be extended by increasing its power using the variable power amplifier 116. The amplifier 116 provides additional power to the optical head 112 on demand to increase the range of the light signal. For example, the headsets 102 may include a power boost button 130 that is pressed by the user in order to temporarily increase the power of the light signal. If a user receives a power boosted communication, the user may also need to boost his or her own transmitted signal in order for a responsive communication to be received. As such, the headset 102 may be configured to inform the user that a boosted signal has been received and that the use must also boost his or her own signal. For example, the boosted light signal from User A could include a signal boost indicator as part of the data being transmitted that is automatically included when User A boosts his signal. When User B's headset 102 receives that signal, it can inform User B that they should also boost their signal. This might be in the form of an indicator light that is activated in response to a boosted signal and that is visible to User B. This indicator light may be provided in a heads-up display (HUD) configured to be attached or communicatively associated with the headset 102 or another indicator viewable to the user (e.g., an arm-mounted display, light array, etc.).

Figure 15:
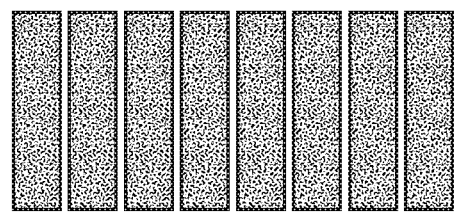
FIGS. 13-15 depict visual displays for providing a user with information related to signals they are receiving or transmitting according to an embodiment of the present disclosure.
Figure 14:
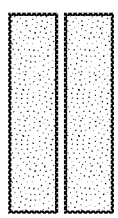
Figure 13:
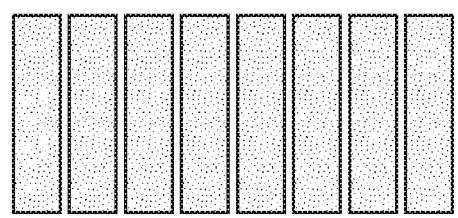

In addition to notifying the user of the need to boost a transmission signal, a HUD may provide a wide range of other information to the user. For example, the display may provide incoming and outgoing signal strength as well as other parameters related to the communications being received or transmitted. For example, whether a message being received is encrypted or non-encrypted, whether the user's own transmissions are encrypted or non-encrypted, how many users are part of the communications link and their identity, etc. An example HUD display is shown in FIGS. 13-15. In this example, the signal strength of an incoming or outgoing message is represented by the number of bars and its encryption status is determined by the shading of the bars, where light shading represents a non-encrypted signal and dark shading represents an encrypted signal. FIG. 13 shows a strong non-encrypted signal, FIG. 14 shows a weak non-encrypted signal, and FIG. 15 shows a strong encrypted signal.

On the other hand, User B's headset 102 may be designed to automatically boost its light signal for a set period of time, in response to the signal strength received from User A, or until another event occurs or condition is met. For example, the headset 102 may automatically boost the light signal until an incoming light signal does not include a signal boost indicator.

In the case of User A-User C communications, a communication link may be established by widening the FOV to angle $\alpha_B$ that is greater than angle $\alpha$. As previously mentioned, this will reduce the range of the light signal, but will widen the FOV. Widening the FOV enables a single user (e.g., User A) to simultaneously communicate with multiple other users (e.g., Users C and D as depicted in FIG. 6).

Referring to FIG. 5, with regard to User A-User D communications, a simple way to form a communication link is for User D to turn around to face User A. This is shown in FIG. 6. However, User D may not know that User A is attempting to communicate with him. Also, because ear protection headsets 102 are typically used in very loud environments, User D may be unable to hear User A, even if User A were to raise his voice.

Figure 7:
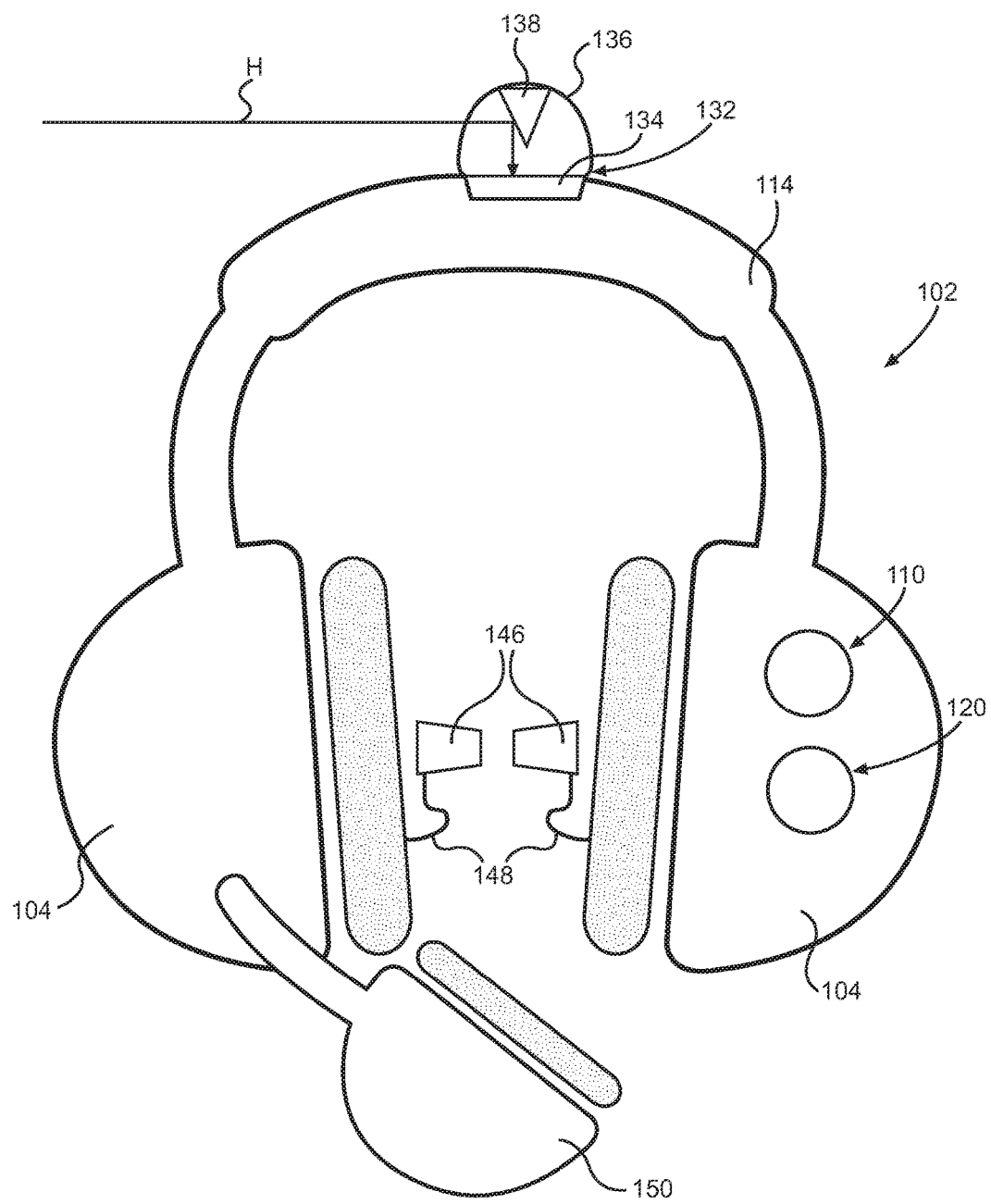
FIG. 7 depicts a headset having a secondary optical receiver, secondary hearing protection, and a mask microphone.

According to one embodiment of the invention, this problem can be solved by sending a "hail" signal to User D so that he knows to turn around. To accomplish this, the headset 102 may be provided with one or more second optical receivers that may or may not be directional so as to provide different areas of coverage around the user. For example, as shown in FIG. 7, a secondary optical receiver 132 may be mounted to the headset 102 and functions as a hail signal detector for the purpose of receiving messages that are not received by the front-facing optical receiver 120. In certain embodiments, the secondary optical receiver 132 is mounted to the headband 114 of the headset 102 and arranged such that it is rear facing for the purpose of receiving hail messages that are transmitted behind the user. Once that message is received, the hail signal is broadcast within the hearing protection cups 104 of the receiving headset 102. That message may include a verbal instruction or aural indicator informing the user to turn around. When wearing the receiving headset 102, a user who hears the hail signal and can know to turn around in order to communicate.

Figure 8:
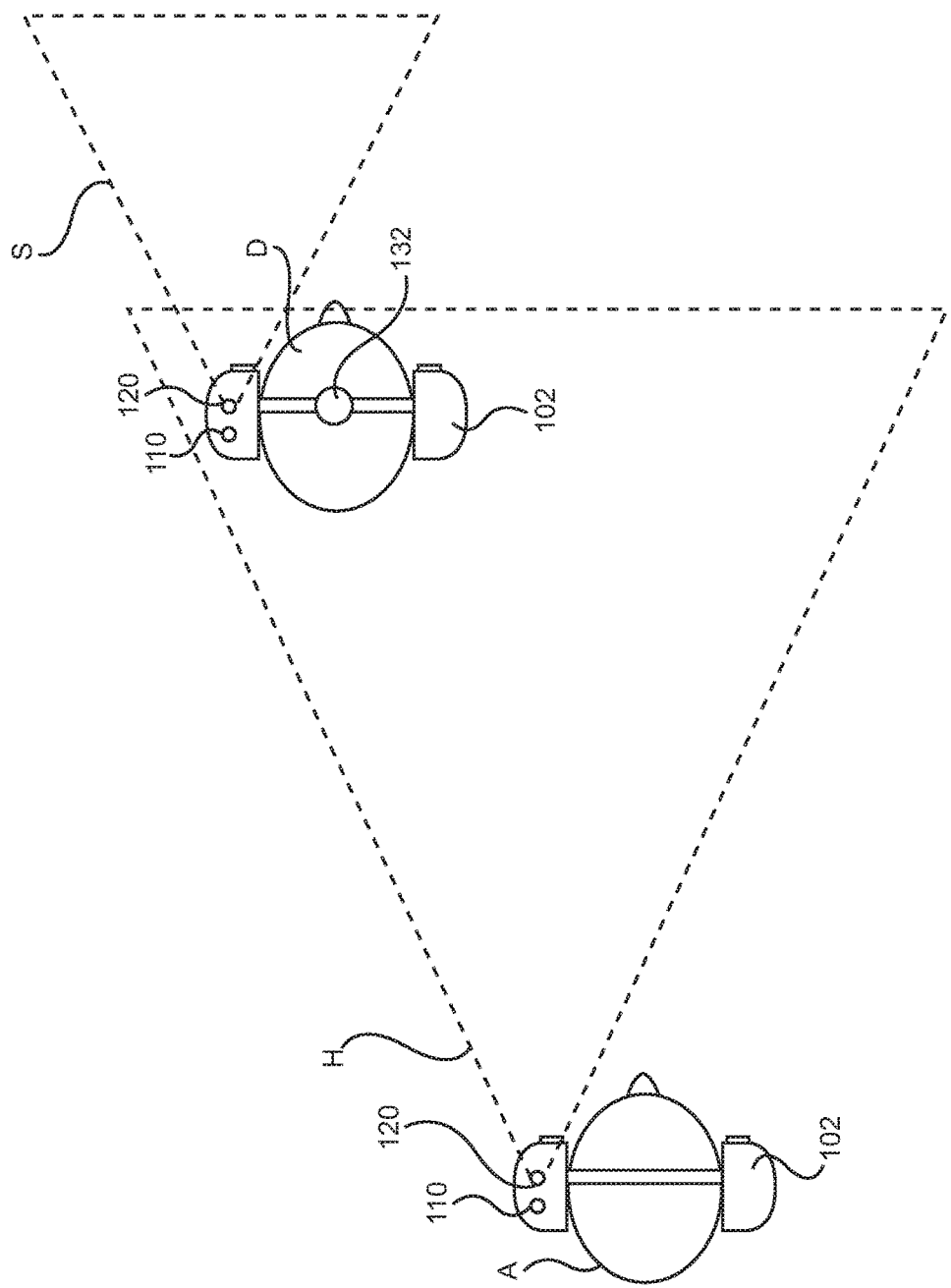
FIG. 8 is a depiction of a User A sending a hail signal to User D to cause User D to turn towards User A to form a complete audio duplex connection.

The secondary optical receiver 132 includes an optical detector 134, a dome optic 136 mounted over the receiver, and a cone reflector 138 mounted within the dome optic 136 and above the optical receiver 132. According to one aspect of the invention, to communicate with User D, User A first sends a hail signal H to User D. If User D is facing away from User A, that signal is not received by the front-facing receiver 120. Instead, it is received by the rear-facing second optical receiver 132, which is located on top of the headset 102. Specifically, the hail signal H enters the second optical receiver 132 through the dome optic 136 and is reflected off of the cone reflector 138 onto the optical detector 134. A benefit of the cone reflector 138 is its wide receiving angle for receiving incoming signals. As shown in FIG. 8, when User A sends a hail signal to User D in the manner described above, a one-way communications channel is created because User A can communicate to User D but User D cannot communicate with User A. User A can communicate a message, such as a hail signal H, to User D. That hail signal H is received by the rear-facing optical receiver 132 of User D's headset 102, because the receiver is oriented so that its receiving field-of-view is within the broadcast field-of-view and the broadcast range of User A's headset. However, User D cannot communicate with User A because User A's front-facing optical receiver 120 is not within the broadcast field-of-view and range of the signal S transmitted by User D's optical transmitter 110. In other words, User D cannot communicate with User A because the headsets are not correctly aligned to enable the light transmitted by the transmitter 110 of User D's headset 102 to be received by the front-facing receiver 120 of User A's headset. In order for User D to send a communication to User A, he must turn to face User A so that a two-way communication link is formed.

Referring back to FIG. 6, from a security and privacy standpoint, there are advantages to having an adjustable-width beam angle. Communications are only received by a user when a communication link is formed with that user. By varying the width of the light signal, the number of people receiving any particular communication can be changed. For example, when User A has a wide light signal having width $\alpha_U$, the headset 102 is operating in a multi-recipient setting because multiple users (e.g., User C and User D) are within the range and FOV of the light signal and receive the communication. The number of users that receive a message may be reduced by changing the beam width. If User A narrows the light signal to width $\alpha$, User C is outside of the FOV and only Users B and D receive the communication. If User A narrows the light signal further to width $\alpha_N$, User C and User D are outside of the FOV and only User B receives the communication. Thus, communications can be made more private and secure by limiting the number of people that receive them by adjusting the beam width. Additionally, communications can be segregated and secured by sending them on different channels. The optical head 112 broadcasts outgoing light signals at one selected wavelength at a time. Communication links may be formed only when a transmitter transmits light and a receiver receives light at matching wavelengths. If a front-facing optical receiver 120 does not receive communications at the selected wavelength, a communication link is not formed and the message will not be communicated to that headset 102.

The optical head 112 and the optical receivers 120, 132, 144 may be configured to operate at a single wavelength continuously over time or at different wavelengths that vary over time, or a combination. A user may communicate on a different channel by selecting a different light wavelength. Wavelength may be changed manually by a user using a channel selector button 154, which may be located on the headset 102 or on the user's person. In some cases, the light maintains the selected wavelength until changed by the user. In other embodiments, activating the channel selector button 154 (or a different button in other embodiments) causes an optional coding-decoding module 158 to modify the light signal. The coding-decoding module automatically changes the wavelength of the light so that it hops from one wavelength to another wavelength and, thereby, encrypts the light signal.

By switching between various wavelengths, communication links may be formed only between selected headsets 102 where the acceptable transmission and reception wavelengths are in sync. Spread spectrum is a similar modulation technique used in radio communications where messages transmitted at various frequencies. Thus, communications can be selectively sent to only certain headsets 102 where the receivers 120, 132, 144 are receptive to light having a wavelength that matches the wavelength of the communication. When receiving an encoded message, activating the coding-decoding module 158 causes the optical receiver to receive light at corresponding wavelengths, which causes the light signal to be broadcast at continuously-changing frequencies. Headsets 102 may be preprogrammed with instructions for synchronized wavelength switching. Alternatively, instruction for switching wavelengths may be provided from one headset to another as part of the light signal.

Additional optional features of the headset 102 are depicted in FIG. 7. The headset 102 may include secondary hearing protection 146 located within the hearing protection cups 104 for providing added hearing protection. The secondary hearing protection 146 may be ear plugs connected via a connector 148 to the inner portion of the hearing protection cups. In some embodiments, the secondary hearing protection 146 may also be configured to output sound waves, such as transmissions received from other users. Therefore, the secondary hearing protection may be integrated with the speakers 122 described above. In this embodiment, the second hearing protection 146 is functioning as an in-ear monitor or headphone (which may alternately be referred to as an "ear bud"). The ear buds may also be provided with noise cancelling electronics having ANR. Active noise reduction technology is well-known and a further discussion of the precise structure utilized is not provided in this description. Another method for reducing ambient noise in the audio signals transmitted between users is to form the microphone 106 (FIG. 3) into a mouth-enclosing mask 150, which reduces ambient noise introduced into the electro-optical signal.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A communications headset system comprising:
   first and second headsets with integrated hearing protection for enabling users to wirelessly communicate when the hearing protection is engaged, each headset configured for placement onto a user's head and having:
   hearing protection cups mounted to the headset and configured to engage a user's ears and to attenuate incoming sound waves that are external to the headset;
   a first optical receiver configured to detect a light signal within a first receiving field-of-view and to generate an incoming electrical signal that corresponds to the light signal, wherein the first receiving field of view is forward-facing;
   a second optical receiver comprising a second receiving field-of-view, wherein the second receiving field-of-view is rearward-facing and at least partially outside of the first receiving field-of-view and wherein the second optical receiver is configured to detect the one or more light signals within the second receiving field-of-view and to generate the incoming electrical signal therefrom;
   a speaker in electrical communication with the first optical receiver and configured to convert the incoming electrical signal to an incoming audio signal and to output the incoming audio signal as sound waves;
   a microphone configured to receive and convert outgoing sound waves to an outgoing electrical signal; and
   an optical transmitter in electrical communication with the microphone configured to receive and convert the outgoing electrical signal to one or more light signals and to broadcast the one or more light signals within a broadcast field-of-view and a broadcast range.

2. A communications headset system comprising:
   first and second headsets with integrated hearing protection for enabling users to wirelessly communicate when the hearing protection is engaged, each headset configured for placement onto a user's head and having:
   hearing protection cups mounted to the headset and configured to engage a user's ears and to attenuate incoming sound waves that are external to the headset;
   a first optical receiver configured to detect a light signal within a first receiving field-of-view and to generate an incoming electrical signal that corresponds to the light signal;
   a second optical receiver comprising a second receiving field-of-view, wherein the second receiving field-of-view is at least partially outside of the first receiving field-of-view and wherein the second optical receiver is configured to detect the one or more light signals within the second receiving field-of-view and to generate the incoming electrical signal therefrom;
   wherein the secondary optical receiver comprises an optical detector, a dome optic mounted over the receiver, and a cone reflector mounted within the dome optic and above the optical receiver, wherein the one or more light signals pass through the dome optic so as to be reflected off of the cone reflector into the optical detector;
   a speaker in electrical communication with the first optical receiver and configured to convert the incoming electrical signal to an incoming audio signal and to output the incoming audio signal as sound waves;
   a microphone configured to receive and convert outgoing sound waves to an outgoing electrical signal; and
   an optical transmitter in electrical communication with the microphone configured to receive and convert the outgoing electrical signal to one or more light signals and to broadcast the one or more light signals within a broadcast field-of-view and a broadcast range.

3. A communications headset system comprising:
   first and second headsets with integrated hearing protection for enabling users to wirelessly communicate when the hearing protection is engaged, each headset configured for placement onto a user's head and having:
   hearing protection cups mounted to the headset and configured to engage a user's ears and to attenuate incoming sound waves that are external to the headset;
   a first optical receiver configured to detect a light signal within a first receiving field-of-view and to generate an incoming electrical signal that corresponds to the light signal;
   a speaker in electrical communication with the first optical receiver and configured to convert the incoming electrical signal to an incoming audio signal and to output the incoming audio signal as sound waves;
   a microphone configured to receive and convert outgoing sound waves to an outgoing electrical signal;
   an optical transmitter in electrical communication with the microphone configured to receive and convert the outgoing electrical signal to one or more light signals and to broadcast the one or more light signals within a broadcast field-of-view and a broadcast range; and
   an amplifier for selectively increasing or decreasing the broadcast range of the optical transmitter, wherein the optical transmitter is configured to incorporate a signal boost indicator into the one or more light signals when the amplifier selectively increases the broadcast range beyond a default range.

4. The system of claim 3 further comprising a visual indicator that is configured to be viewable when the signal boost indicator is received by the headset.

5. The system of claim 3 wherein the optical transmitter is configured to automatically increase the broadcast range of the one or more light signal using the amplifier in response to the first optical receiver receiving the signal boost indicator.

6. A communications headset system comprising:
   first and second headsets with integrated hearing protection for enabling users to wirelessly communicate when the hearing protection is engaged, each headset configured for placement onto a user's head and having:

hearing protection cups mounted to the headset and configured to engage a user's ears and to attenuate incoming sound waves that are external to the headset;

a first optical receiver configured to detect a light signal within a first receiving field-of-view and to generate an incoming electrical signal that corresponds to the light signal;

a speaker in electrical communication with the first optical receiver and configured to convert the incoming electrical signal to an incoming audio signal and to output the incoming audio signal as sound waves;

a microphone configured to receive and convert outgoing sound waves to an outgoing electrical signal; and an optical transmitter in electrical communication with the microphone configured to receive and convert the outgoing electrical signal to one or more light signals and to broadcast the one or more light signals within a broadcast field-of-view and a broadcast range;

wherein each headset includes an integrated mask configured to selectively engage a mouth of the user for attenuating incoming sound waves external to the mask, wherein the microphone is disposed within the mask.

7. A method for providing selective communication between a plurality of users using free-space optics:

A. providing first and second headsets, each headset having an input-output module having a broadcast field-of-view, broadcast range, and receiving field-of-view;

B. engaging a user hearing protection feature of each of the headsets;

C. forming a communications link between the headsets by positioning the receiving field-of-view of the first headset within the broadcast field-of-view and broadcast range of the second headset;

D. converting outgoing sound waves of a user of the second headset to a light signal and emitting the light signal using the second headset;

E. receiving and converting the light signal to an incoming audio signal using the first headset and then broadcasting the incoming audio signal to a user of the first headset;

F. transmitting a hail signal from the second headset to the first headset;

G. in response to the user of the first headset receiving the hail signal, forming a two-way communications link between the first headset and the second headset when the receiving field-of-view of the first headset is within the broadcast field-of-view and range of the second headset and the receiving field-of-view of the second headset is within the broadcast field-of-view and range of the first headset; and H. boosting the light signal to extend the broadcast range of the second headset when the receiving field-of-view of the first headset is outside the broadcast range of an un-boosted light signal.

8. The method of claim 7, further comprising automatically boosting the light signal of the second headset in response to receiving the boosted light signal from the first headset.

9. A communications headset system for providing wireless communication, the system comprising:

a plurality of headsets with integrated hearing protection for enabling users to wirelessly communicate with one another with the hearing protection being engaged, each headset configured for placement onto a user's head and having:

hearing protection mounted to the headset configured to engage a user's ears and to attenuate incoming sound waves external to the hearing protection;

a first audio-to-light transducer for converting an incoming audio signal to a light signal and broadcasting the light signal;

a second audio-to-light transducer having a receiving field-of-view for receiving a light signal, the second audio-to-light transducer configured to convert light signals to an audio signal and further configured to transmit the audio signal to the user;

a third audio-to-light transducer having a receiving field-of-view for receiving a light signal that is at least partially outside the receiving field-of-view of the second audio-to-light transducer, the third audio-to-light transducer configured to convert light signals to an audio signal and further configured to transmit the audio signal to the users; and beam-forming optics configured to adjust one or more parameters of one or more of the first audio-to-light transducer, the second audio-to-light transducer, and the third audio-to-light transducer.

* * * * *